United States Patent [19]

Mitsui et al.

[11] Patent Number: 5,084,470
[45] Date of Patent: Jan. 28, 1992

[54] GERMICIDAL COMPOSITION

[75] Inventors: Susumu Mitsui, Koshigaya; Shigeru Kurose, Misato; Ryoji Funatsu, Tokyo, all of Japan

[73] Assignee: Somar Corporation, Japan

[21] Appl. No.: 602,047

[22] Filed: Oct. 25, 1990

Related U.S. Application Data

[63] Continuation of Ser. No. 488,879, Mar. 6, 1990, abandoned.

[30] Foreign Application Priority Data

Mar. 30, 1989 [JP] Japan .................... 1-80660

[51] Int. Cl.$^5$ .................... A01N 43/26; A01N 43/80
[52] U.S. Cl. .................... 514/372; 514/441
[58] Field of Search .................... 514/372, 441

[56] References Cited

U.S. PATENT DOCUMENTS 4,466,975 8/1984 Magami et al. .................... 424/270

FOREIGN PATENT DOCUMENTS 0282203 of 1988 European Pat. Off. .
57-212107 12/1982 Japan .................... 514/372
60-1105 7/1985 Japan .
60-139601 9/1985 Japan .................... 514/372

OTHER PUBLICATIONS

Chemical Abstracts, vol. 102, No. 23, 10th Jun. 1985, pp. 222-223, Abstract No. 199590v, Columbus, Ohio, U.S.
Patent Abstracts of Japan, vol. 12, No. 159 (C-495) (3006), 14th May 1988.

*Primary Examiner*—Allen J. Robinson
*Attorney, Agent, or Firm*—Lorusso & Loud

[57] ABSTRACT

A germicidal composition includes 3-isothiazolone compound of the general formula (I):

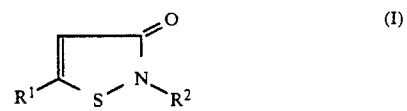

wherein $R^1$ represents a hydrogen atom or a halogen atom and $R^2$ represents a hydrogen atom or an alkyl group, and 4,5-dichloro-1,2-dithiole-3-one of the formula (II):

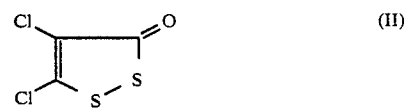

4 Claims, No Drawings

GERMICIDAL COMPOSITION

This application is a continuation of application Ser. No. 07/488,879, filed Mar. 6, 1990, now abandoned.

This invention relates generally to a germicide and, more specifically, to a germicidal composition suitable for preventing growth of various germs such as yeasts and filamentous fungi in industrial water such as waste water from pulp mills or cooling water for heat exchangers.

In industrial water such as waste water from paper making steps in pulp-related industries and recirculating cooling water used in various mills, microorganisms such as germs, fungi and bacteria are apt to grow and to cause various problems.

For example, filamentous fungi and yeasts are apt to grow in industrial water used in paper or pulp mills and to form slime within water passages such as pipe walls having roughened surfaces and other portions such as chests and flow boxes through which the water is passed at a low flow rate. The accumulated slimes occasionally depart from their depositing surfaces to cause contamination of paper and pulp products. Other industrial products such as aqueous coating materials, polymer latex, bonding agents, metal machining oils, hides and skins also encounter similar problems. Further, accumulation of slimes also cause blockage of water passages and reduction of heat transfer efficiency.

To cope with these problems, there have been hitherto used organometallic compounds, chlorinated organic compounds, sulfur-containing organic compounds and quarternary ammonium compounds for the prevention of growth of germs in industrial water. These known germicides, however, have certain problems. That is, the known organometallic compounds and chlorinated organic compounds must be used in a large amount in order to obtain satisfactory germicidal effects. This causes environmental pollution. The known sulfur-containing organic compounds and quarternary ammonium compounds cause a problem of generation of unpleasant odor. Some of these compounds also cause a problem of foaming of the water to which they are added.

Japanese Examined Patent Publication (Tokkyo Kokoku) No. Sho-52-14,295 discloses a germicide containing 4,5-dichloro-1,2-dithiole-3-one. This germicide is effective only to limited kinds of germs, has not sufficient germicidal activity and lacks durability in germicidal effect. Japanese Published Unexamined Patent Application (Tokkyo Kokai) No. Sho-60-1105 discloses a germicide containing 4,5-dichloro-1,2-dithiole-3-one and a metal complex of a 3-isothiazolone compound. While the conjoint use of these two compounds provides a synergistic effect, the germicidal effect is still not fully satisfactory.

The present invention has been made with the foregoing problems of the conventional germicides in view. There is provided in accordance with the present invention a germicidal composition comprising 3-isothiazolone compound of the general formula (I):

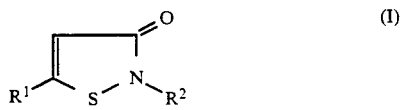

wherein $R^1$ represents a hydrogen atom or a halogen atom and $R^2$ represents a hydrogen atom or an alkyl group, and 4,5-dichloro-1,2-dithiole-3-one of the formula (II):

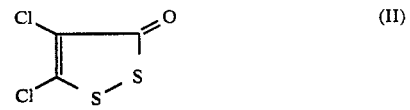

The present inventors have found that when the isothiazolone compound of the formula (I) is used, as a free state rather than as a metal complex, together with the compound of the formula (II), a remarkably higher synergistic effect is obtainable than that obtained by the conjoint use of the corresponding isothiazolone metal complex with the compound of the formula (II). This is surprising since the germicidal activity of the isothiazolone compound (I) is comparable to that of the corresponding metal complex thereof. The germicidal composition according to the present invention also exhibits its germicidal effect for a long period of time against a wide variety of germs including filamentous fungi and yeasts.

The present invention will now be described in detail below.

In the general formula (I), the group $R^1$ is preferably a hydrogen atom or a chlorine atom and the group $R^2$ is preferably a hydrogen atom or an alkyl group having 1-8 carbon atoms. Illustrative of suitable isothiazolone compounds (I) are 2-methyl-3-isothiazolone, 5-chloro-2-methyl-3-isothiazolone, 2-octyl-3-isothiazolone and 2-ethyl-3-isothiazolone.

The compounds of the formulas (I) and (II) are used in such a proportion that the weight ratio of the compound (I) to the compound (II) is 1:10 to 10:1, preferably 1:5 to 5:1.

The germicidal composition of the present invention may be in the form of a solution, a dispersion or an emulsion. Thus, a suitable liquid medium, which may be aqueous or organic, may be used for dissolving, dispersing or emulsifying the first and second ingredients. An emulsifier such as a surfactant or a stabilizer may be also used to stabilize the dispersion or emulsion. Examples of organic media include alcohols, ketones, ethers and hydrocarbons. If desired, the germicidal composition may be supported on a solid carrier.

Because of its high synergistic effect, a low concentration of the composition of the present invention can exhibit satisfactory germicidal activities. Thus, for example, when the composition is used for incorporation into industrial water of paper or pulp mills, a concentration of 0.01–100 ppm (calculated as a total amount of the compounds of the formulas (I) and (II)) is sufficient to obtain desired effect. For incorporation into industrial water for use in the field of aqueous coating materials, bonding starch or hides and skins, the concentration is generally 1–500 ppm.

The following examples will further illustrate the present invention. In the examples, "part" and "%" are by weight.

Example 1

A germicide having the following composition was prepared:

| | |
|---|---|
| 2-Methyl-3-isothiazolone | 5 parts |

-continued

| | |
|---|---|
| 4,5-Dichloro-1,2-dithiole-3-one | 5 parts |
| Ethylene glycol | 88 parts |
| SORPOL 900A* | 2 parts |

*Anionic surfactant, manufactured by Toho Kagaku K. K.

Example 2

A germicide having the following composition was prepared:

| | |
|---|---|
| 5-Chloro-2-methyl-3-isothiazolone | 5 parts |
| 4,5-Dichloro-1,2-dithiole-3-one | 5 parts |
| Ethylene glycol | 88 parts |
| SORPOL 900A | 2 parts |

Example 3

A germicide having the following composition was prepared:

| | |
|---|---|
| 5-Chloro-2-methyl-3-isothiazolone | 4 parts |
| 2-Methyl-3-isothiazolone | 1 part |
| 4,5-Dichloro-1,2-dithiole-3-one | 5 parts |
| Ethylene glycol | 88 parts |
| SORPOL 900A | 2 parts |

Example 4

A germicide having the following composition was prepared:

| | |
|---|---|
| 2-Octyl-3-isothiazolone | 5 parts |
| 4,5-Dichloro-1,2-dithiole-3-one | 5 parts |
| Ethylene glycol | 88 parts |
| SORPOL 900A | 2 parts |

Comparative Example 1

A germicide having the following composition was prepared:

| | |
|---|---|
| 2-Methyl-3-isothiazolone | 10 parts |
| Ethylene glycol | 88 parts |
| SORPOL 900A | 2 parts |

Comparative Example 2

A germicide having the following composition was prepared:

| | |
|---|---|
| 5-Chloro-2-methyl-3-isothiazolone | 10 parts |
| Ethylene glycol | 88 parts |
| SORPOL 900A | 2 parts |

Comparative Example 3

A germicide having the following composition was prepared:

| | |
|---|---|
| 2-Methyl-3-isothiazolone | 2 parts |
| 5-Chloro-2-methyl-3-isothiazolone | 8 parts |
| Ethylene glycol | 88 parts |
| SORPOL 900A | 2 parts |

Comparative Example 4

A germicide having the following composition was prepared:

| | |
|---|---|
| 4,5-Dichloro-1,2-dithiole-3-one | 10 parts |
| Ethylene glycol | 88 parts |
| SORPOL 900A | 2 parts |

Comparative Example 5

A germicide having the following composition was prepared:

| | |
|---|---|
| 2-Octyl-3-isothiazolone | 10 parts |
| Ethylene glycol | 88 parts |
| SORPOL 900A | 2 parts |

Comparative Example 6

A germicide having the following composition was prepared:

| | |
|---|---|
| 2-Methyl-3-isothiazolone magnesium nitrate complex | 1 part |
| 5-Chloro-2-methyl-3-isothiazolone magnesium nitrate complex | 4 part |
| 5-Chloro-2-methyl-3-isothiazolone | 5 parts |
| Ethylene glycol | 88 parts |
| SORPOL 900A | 2 parts |

The above compositions were subjected to the following tests for evaluating their germicidal properties.

Activity Test

The following germs were used (Indicated in the brackets are abbreviations):

| | |
|---|---|
| *Pseudomonas aeruginosa* | (P.a) |
| *Aerobactor aerogenes* | (A.a) |
| *Bacillus subtilis* | (B.s) |
| *Alcaligenes viscosus* | (A.v) |
| *Aspergillus niger* | (A.n) |
| *Geotrichum sp.* | (G.s) |

Each germ was suspended in an aqueous culture medium containing 0.1% peptone, 0.05% glucose, 0.01% potassium hydrogen phosphate and 0.005% magnesium sulfate. A predetermined amount of the suspension was sampled in test tubes to which a predetermined amount (5, 10, 20, 40 and 80 ppm) of the germicidal composition to be tested was mixed. The mixture was cultured with shaking at 32° C. for 24 hours. Thereafter, the degree of growth of the germ was measured by measurement of turbidity. The minimum concentration of the germicidal composition which perfectly prevented the growth of the germ was as shown in Table 1. Each germ was found to grow upon culturing in the absence of the germicide.

TABLE 1

| Example | P.a | A.a | B.s | A.v | A.n | G.s |
|---|---|---|---|---|---|---|
| 1 | 10 | 10 | 5 | 10 | 10 | 10 |
| 2 | 10 | 5 | 5 | 5 | 10 | 10 |
| 3 | 5 | 5 | 5 | 5 | 5 | 5 |
| 4 | 10 | 10 | 10 | 10 | 5 | 5 |
| Comp. 1 | 80 | 80 | 40 | 80 | 80 | 80 |
| Comp. 2 | 40 | 40 | 20 | 40 | 80 | 80 |

TABLE 1-continued

| Example | P.a | A.a | B.s | A.v | A.n | G.s |
|---|---|---|---|---|---|---|
| Comp. 3 | 40 | 40 | 20 | 40 | 40 | 40 |
| Comp. 4 | 40 | 80 | 40 | 80 | 80 | 40 |
| Comp. 5 | 80 | 80 | 80 | 80 | 40 | 40 |
| Comp. 6 | 20 | 20 | 20 | 20 | 20 | 20 |

From the results shown in Table 1, it will be appreciated that the germicidal compositions of the present invention can prevent any of the tested germs from growing with a low concentration of 10 ppm or less.

Growth Preventing Test (1)

To a recirculating white liquor used in a paper making step of a paper mill was added each of the above germicidal compositions three times per day (2 hours in one time) so that the concentration of the germicide in the white liquor was maintained at 20 ppm. The test was carried out continuously for 7 days. Then the white liquor was sampled to measure the number of germ cells. Thus, the sampled white liquor was diluted with sterilized water and poured into a glass tray in a predetermined amount, to which a Waxman agar culture medium was poured. After gentle mixing, the mixture was allowed to be solidified with a flattened surface and placed in an incubator at 32° C. for 2 days for culturing. Then the colony was counted by a colony counter to give the results shown in Table 2. During the 7 days test, the number of the occurrence of paper breakage in the paper making step was counted. The results are also shown in Table 2.

TABLE 2

| Example No. | Number of Cells (per 1 ml) | Number of Occurrence of Paper Breakage |
|---|---|---|
| 1 | $10^2$ or less | 0 |
| 2 | $10^2$ or less | 0 |
| 3 | $10^2$ or less | 0 |
| 4 | $10^2$ or less | 0 |
| Comp. 1 | $5.2 \times 10^8$ | 10 |
| Comp. 2 | $3.8 \times 10^6$ | 8 |
| Comp. 3 | $2.8 \times 10^5$ | 6 |
| Comp. 4 | $2.3 \times 10^5$ | 7 |
| Comp. 5 | $5.4 \times 10^7$ | 9 |
| Comp. 6 | $8.6 \times 10^4$ | 4 |
| Control* | over $10^8$ | 15 |

*no germicide was used.

Growth Preventing Test (2)

To an aquous paper coating liquid (pH 9.0) of a starch type was added a bouillon liquid medium and a previously rotted, paper coating liquid, to which was added to each of the germicidal compositions to a concentration of 300 ppm. The resulting mixture was incubated at 32° C. for 5 days and the number of the living cells was counted. The results are shown in Table 3.

TABLE 3

| Example No. | Number of Cells (per 1 ml) |
|---|---|
| 1 | $10^2$ or less |
| 2 | $10^2$ or less |
| 3 | $10^2$ or less |
| 4 | $2.6 \times 10^2$ |
| Comp. 1 | $4.5 \times 10^6$ |
| Comp. 2 | $3.8 \times 10^6$ |
| Comp. 3 | $8.8 \times 10^6$ |
| Comp. 4 | $5.2 \times 10^6$ |
| Comp. 5 | $4.6 \times 10^8$ |
| Comp. 6 | $4.0 \times 10^5$ |
| Control* | over $10^8$ |

*no germicide was used

What is claimed is:

1. A germicidal composition consisting essentially of a synergistic effective amounts of 3-isothiazolone compound of the formula (I):

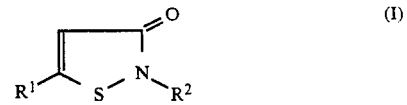

wherein said 3-isothiazolone compound is in its free state and wherein $R^1$ represents a hydrogen atom or a halogen atom and $R^2$ represents a hydrogen atom or an alkyl group having 1–8 carbon atoms, and 4,5-dichloro-1,2-dithiole-3-one of the formula (II):

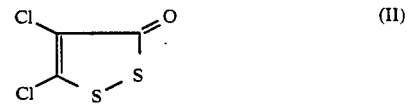

2. A germicidal composition according to claim 1, wherein the weight ratio of the 3-isothiazolone compound to the 4,5-dichloro-1,2-dithiole-3one is 1:10 to 10:1.

3. A germicidal composition according to claim 1, wherein the weight ratio of the 3-isothiazolone compound to the 4,5-dichloro-1,2-dithiole-3-one is 1:5 to 5:1.

4. A germicidal composition according to claim 1, further comprising a liquid medium in which the 3-isothiazolone compound and the 4,5-dichloro-1,2-dithiole-3-one are dissolved, dispersed or emulsified.

* * * * *